(12) United States Patent
Li et al.

(10) Patent No.: US 6,479,418 B2
(45) Date of Patent: Nov. 12, 2002

(54) POROUS CERAMIC BODY

(75) Inventors: Shihong Li, Utrecht (NL); Klaas de Groot, Heemstede (NL); Pierre Jean F. Layrolle, Utrecht (NL); Clemens Antoni van Blitterswijk, Hekendorp (NL); Joost Robert de Wijn, Nijmegen (NL)

(73) Assignee: IsoTis N.V., Bilthoven (NL)

( * ) Notice: Subject to any disclaimer, the term of this patent is extended or adjusted under 35 U.S.C. 154(b) by 21 days.

(21) Appl. No.: 09/738,880

(22) Filed: Dec. 15, 2000

(65) Prior Publication Data

US 2002/0037799 A1 Mar. 28, 2002

(30) Foreign Application Priority Data

Dec. 16, 1999 (EP) .............................................. 99204378

(51) Int. Cl.⁷ .......................... C04B 38/06; A61L 37/12
(52) U.S. Cl. .............................. 501/81; 501/82; 501/83; 106/35; 623/23.56
(58) Field of Search .............................. 501/81, 82, 83; 106/35; 623/23.56

(56) References Cited

U.S. PATENT DOCUMENTS 4,654,314 A * 3/1987 Takagi et al. .................. 364/44
5,171,720 A * 12/1992 Kawakami .................... 501/80
6,283,997 B1 * 9/2001 Garg et al. ............... 623/16.11
6,316,091 B1 * 11/2001 Richart et al. ............... 264/321

FOREIGN PATENT DOCUMENTS

| GB | 1033560 | 6/1996 |
| GB | 2317887 | 4/1998 |

OTHER PUBLICATIONS

Toyo Rubber Industry, "Manufacture of porous ceramic body," *Chemical Abstracts*, 102(14):310, 1985, abstract No. 118385g, XP002183030 & JP 59 190250 A.
Nagai et al., "Ceramic foam bodies," *Chemical Abstracts*, 104(18):345, 1986, abstract No. 154446c, XP002138031 & JP 60 200874 A.
Yasuaki, Sharp Corp., "Preparation of Adsorption of Catalyst Material," *Patent Abstracts of Japan*, JP pub. No. 09108567, 1997, abstract.
Yoshinori, Japan Steel Works Ltd., "Production of Porous Calcium Phosphate Sintered Compact," *Patent Abstracts of Japan*, JP pub. No. 05294752, 1993, abstract.

* cited by examiner

*Primary Examiner*—C. Melissa Koslow
(74) *Attorney, Agent, or Firm*—Banner & Witcoff, Ltd.

(57) ABSTRACT

The invention relates to a process for preparing a porous ceramic body, which process is based on a negative replica method. The invention further relates to a ceramic body obtainable by said method and to its use as a scaffold for tissue engineering.

11 Claims, 4 Drawing Sheets

POROUS CERAMIC BODY

The invention relates to a method of preparing a porous ceramic body and to a body obtainable by said method. The invention further relates to the use of said body as a scaffold in tissue engineering.

Regeneration of skeletal tissues has been recognized as a new means for reconstruction of skeletal defects arising from abnormal development, trauma, tumors and other conditions requiring surgical intervention. Autologous bone grafting is considered the gold standard of bone transplantation with superior biological outcomes. However, autologous bone stocks are limited and often insufficient, particularly when large skeletal defects are encountered. Allografts are used as alternative materials but are associated with immunologically mediated complications and risks of disease transmission. Additional disadvantages of autograft and allograft materials include their limited potential for molding or shaping to achieve an optimum fit with bone voids.

As surgical techniques and medical knowledge continue to advance, there is an increasing demand for synthetic bone replacement materials, resulting from the limited supply of autograft materials and the health risks associated with the use of allografts. Hydroxyapatite has been investigated for use in the osseous environment for over 20 years, and the biocompatibility of the ceramic and its osteoconductive behavior is well established. Since porous HA is more resorbable and more osteoconductive than dense HA, there is an increasing interest in the development of synthetic porous hydroxyapatite (HA) bone replacement materials for the filling of both load-bearing and non-load-bearing osseous defects. Such technology could have the potential for restoration of vascularization and complete penetration of osseous tissue throughout the repair site.

Variation of the scaffold design as three-dimensional superstructures has been demonstrated as an approach to optimize the functionality of bone regeneration materials so that these materials may be custom designed for specific orthopedic applications in the form of void fillers, implants, or implant coatings. In attempt to develop a skeletal cell and tissue carrier, which could provide optimal spatial conditions for cell migration and maintenance by the arrangement of structural elements such as pores and fibers, the feasibility of using "live" material is under investigation. Such live material could take the form of an open-porous implant system together with living tissue. In other words, this is so-called hard tissue engineering.

The most traditional way of preparing a porous HA ceramic is to use a foaming agent like hydrogen peroxide ($H_2O_2$). In detail, an HA slurry is made by mixing HA powder with water and a $H_2O_2$ solution. Then, samples of the slurry are put in oven, under elevated temperature. $H_2O_2$ decomposes and $O_2$ is released from the bulk material, leaving a porous structure. Until today, this technique is still widely used in both clinical applications and research areas. However, porous ceramics made by this $H_2O_2$ method has an intrinsic shortcoming: it possesses only "laminar porosity". In other words, the pores are interconnected mostly in a laminar way, so there is no truly three-dimensional interconnected structure.

Slip-casting is another way of synthesizing porous ceramics. The manufacturing route comprises preparing an HA slurry (slip) by mixing HA powder under stirring with water, a deflocculant and binder agents. In this slurry, a kind of foam (sponge) is immersed and pressed. As a result, the slurry will be sucked into the foam. A layer of ceramic will be coated on all the struts of the sponge after removing the extra slurry by squeezing the samples. Then the samples will be dried in microwave oven and finally sintered in a furnace. This method is often referred to as a positive replica method.

Slip-casted materials are highly porous; they have a reticulate structure. However, due to the inner flaws in the ceramic, which are left after the sponge is burnt off, the strength of the material can not be increased to meet the requirement of tissue engineering application.

Meanwhile, coral HA has gained a wide interest in biomaterial spheres. An example of such a material is Interpore®, which has a high porosity and excellent microporous surface structure. However, it is an expensive material and, more importantly, its mechanical strength is insufficient for tissue engineering applications.

In summary, there are several known methods of preparing porous ceramics. However, there are specific requirements for porous ceramic which are to be used for skeletal regeneration, hard tissue repairing, and even for hard tissue engineering purpose. For bony tissue ingrowth, it is accepted that the pore size should be in the range of 100 to 300 microns, and the pores should be fully interconnected. This specification gives rise to a desire for a more suitable porous ceramic (tissue carrier or 3-D scaffold).

The present invention provides an improved method for preparing a porous ceramic body. The method leads to a ceramic body having interconnected pores of a controllable pore size. Furthermore, the mechanical properties of the ceramic body are superior to those of ceramic bodies prepared by the above discussed, known methods. Particularly its compressive strength is much higher.

A process for preparing a porous ceramic body according to the invention is based on a negative replica method. More in detail, the present method comprises the steps of:
1) preparing an aqueous slurry of a ceramic material;
2) mixing the slurry with a liquid, viscous organic phase to obtain a dough, wherein the organic phase is substantially insoluble in water, and is thermally decomposable into gaseous residues;
3) drying the dough; and
4) removing the organic phase by thermal decomposition.

The features of various preferred embodiments are discussed below with reference to the accompanying figures in which.

Figure 1:
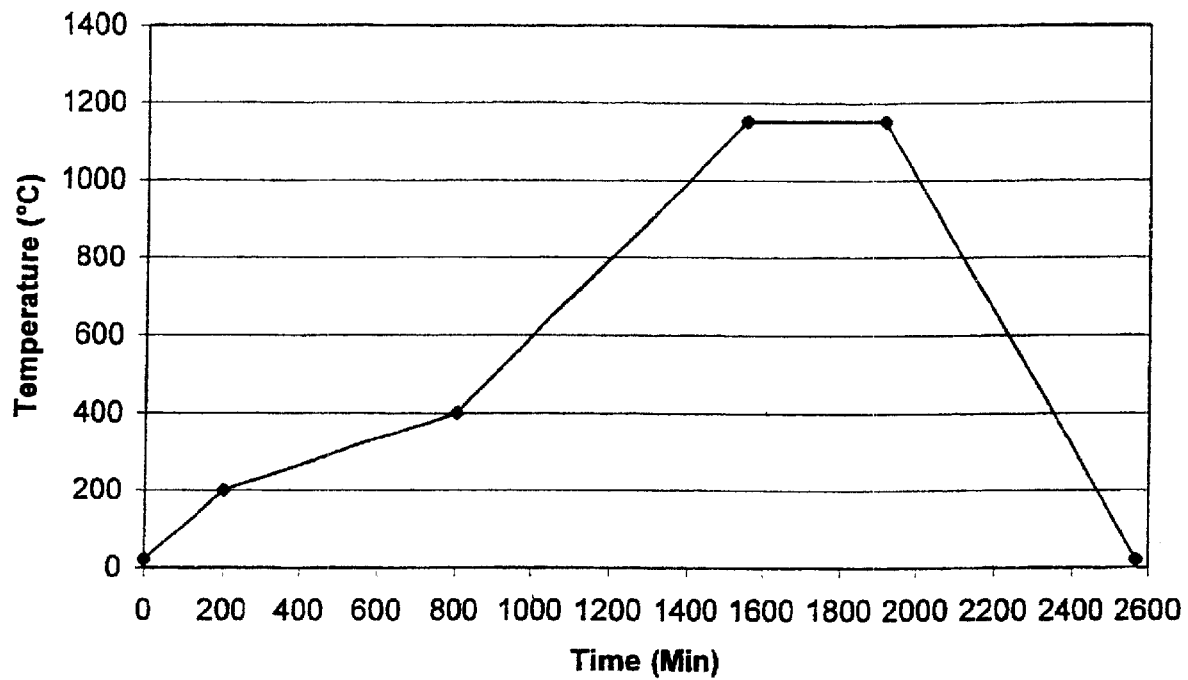
FIG. 1 shows the heating profile used in one embodiment to heat and sinter a body produced in accordance with a preferred embodiment.

As has been mentioned, the present method has the advantage that a ceramic body is obtained which has a porous structure consisting of interconnected pores. Moreover, a particularly high porosity can be achieved while maintaining superior mechanical properties.

In addition, it has been found that a ceramic body obtainable by the present method possesses a specific microporous surface inside the macropores. In other words, the surface of the ceramic body, including the surface within the pores, has a certain advantageous rugosity. By virtue of this feature, a good attachment of cells is obtained when cells are seeded onto the body, e.g. in tissue engineering applications. Also, by virtue of this feature the ceramic body may give rise to osteoinduction. The above described ceramic materials prepared by a slip-casting method have been found not to have this feature.

The ceramic material of which the slurry is prepared can in principle be any material of which it is desired to prepare a porous body of. In other words, the choice for a particular ceramic material will depend on the objective application of the final product. In view of the envisaged application of the porous body as a scaffold in tissue engineering, in accordance with the invention it is preferred that the ceramic material is a calcium phosphate. Highly preferred calcium phosphates may be chosen from the group of octacalcium phosphate, apatites, such as hydroxyapatite and carbonate apatite, whitlockites, α-tricalcium phosphate, β-tricalcium phosphate, sodium calcium phosphate, and combinations thereof.

Under certain circumstances it may be desired to incorporate an additive in the aqueous slurry. Examples of such additives are binders, surfactants, pH controlling agents, deflocculants, and the like. As binder, a water soluble polymer may be used, such as a cellulose derivative (e.g. carboxymethylcellulose) may be used, preferably in an amount of between 0.05 and 0.5 wt. %, based on the weight of the slurry. A pH controlling agent may suitably be employed to control the solubility of the ceramic material. It will be clear that it is to be avoided that (a significant amount of) the ceramic material dissolves in the aqueous phase. The skilled person will be able to determine whether there is a need for the use of a certain additive, based on his general knowledge.

The concentration of the ceramic material in the slurry will depend on the solubility of the chosen ceramic material in water. Generally, said concentration will be chosen between 50 and 80 wt. %, preferably between 55 and 75 wt. %, based on the weight of the slurry. The slurry may be prepared by admixing water and the ceramic material under stirring until a homogeneous slurry is obtained.

As has been mentioned above, the slurry is mixed with an organic phase, which does not dissolve in the slurry (i.e. is substantially insoluble in water) and does not react chemically with the ceramic material in the slurry.

In order to enable a homogeneous distribution of the organic phase throughout the slurry, the organic phase needs to be in a liquid form at the time of mixing. Further, in order to ensure that the resultant mixture has the form of a moldable dough, allowing shaping of the resulting ceramic body, the organic phase should be viscous. It is also possible that the viscosity of the organic phase is relatively low at the time of mixing with the slurry, but increases upon drying.

Another requirement that has to be met by the organic phase is that it should be removable from the dough by thermal decomposition. It is preferred that the organic phase decomposes into volatile and/or gaseous residues upon exposure to temperatures above 200° C. or 400° C. Depending on the envisaged application of the ultimate ceramic body, it is desirable that substantially no charred or tar-like residues are formed upon thermal decomposition, respectively remain within the porous structure of the ceramic body after sintering.

Suitable examples of materials that can be used to form the organic phase will readily be identified by the skilled person, based on the considerations presented above. Depending on the material chosen, an organic solvent may or may not be present. It will be clear that, if an organic solvent is to be used, it should be chosen such that it does not substantially interfere with the characteristics of the organic phase recited above.

Without wishing to be exhaustive, the following suitable materials for use in the organic phase can be mentioned: waxes, shellac, fatty acids, fats, epoxy resins, polyurethane resins, polyester resins, poly(meth)acrylate resins and combinations thereof. Particular good results have been obtained using a poly(meth)acrylate resin. Such a resin can be a homo- or a copolymer of various acrylate and/or methacrylate monomers. Preferably, the resin is polymethylmethacrylate.

When a synthetic polymer is used in the organic phase, it has been found advantageous to incorporate a small amount of monomeric material. This monomeric material may polymerize in situ in-the dough formed by mixing the organic phase with the aqueous slurry of the ceramic material, thereby beneficially affecting the formation of interconnected pores in the final ceramic body. The monomeric material may be included in a ratio of up to 3:1, with respect to the weight of the polymer. Preferred ratios range from 1:1 to 1:2.5 with respect to the weight of the polymer. If necessary, a small amount of a suitable catalyst or initiator enabling the polymerization may be present.

In case it is desired to prepare a ceramic body having a particularly high porosity, a foaming agent may conveniently be included in the organic phase. The foaming agent may be present in the organic phase in amounts of up to 10 wt. %. By use of a foaming agent, it has been found possible to achieve a porosity of about 60%. A preferred example of a foaming agent is a combination of sodium bicarbonate and citric acid, which agents may suitably be employed in a weight ratio of between 1:2 and 1:5. Advantageously, this specific foaming agent substantially only acts when brought into contact with water (i.e. with the aqueous slurry of ceramic material). This has the effect that the organic phase will swell to a certain extent, while said phase will maintain its continuity, so that the mechanical properties of the ceramic body that is being prepared are substantially not adversely affected as a result of the use of a foaming agent.

In another embodiment, combustible particulate matter, such as pine tree branches or rigid polymeric fibers, are incorporated in the organic phase, in the slurry of ceramic material or in the mixture of the organic phase and said slurry. This matter is meant to decompose when the organic phase is removed by thermal decomposition. As a result, a ceramic body is obtained which has discrete cavities in its structure which have the shape and size of the particulate matter that has been removed. Such cavities may advantageously have the shape of tunnels, of channels, which facilitates the flow of culture medium through the ceramic body when it is used as a scaffold in tissue engineering and cells seeded onto it are being cultured.

The aqueous slurry of ceramic material and the organic phase are preferably mixed in a volume ratio of between 1:2 and 3:1, more preferably between 1:1 and 2:1. The dough will preferably comprise at least 35 vol. % of the organic phase, remainder preferably being the aqueous slurry. Both components of the dough may be mixed in any manner, taking care to obtain a homogeneous mixture.

The dough is subsequently dried. It is at this stage that a polymerization reaction may take place in the organic phase, as such is aimed at. Preferably the drying is carried out for a duration of at least 5 hours at atmospheric conditions. If a more thorough drying is desired, a microwave can be used for this purpose. It is further preferred that the dough is molded into a desired shape prior to drying. To this end, the dough may be brought into a mold, which can for instance be a polypropylene or polyethylene mold, or any other material that can be removed by burning substantially without release of toxic gases.

The dried dough is subsequently placed in a furnace in order to thermally decompose, and remove, the organic phase. Suitable conditions will depend on the nature of the organic phase. Typically, thermal decomposition will be achieved at a temperature between 200 and 800° C. In order to ensure that the organic phase substantially completely disappears, the heating may be prolonged for a duration of up to 24 or even 36 hours.

After the thermal decomposition step, a porous ceramic body is obtained which may find application in itself. For many applications, however, it is preferred that the ceramic body is sintered. Sintering may be performed at a temperature between 800 and 1400° C., preferably between 1000 and 1300° C.

The thus obtained ceramic body has superior mechanical properties. In particular, it has a very high strength. The compressive strength will preferably be at least 10 MPa. Furthermore, the ceramic body has a porosity of a very advantageous configuration. The pores are interconnected and preferably have a mean diameter ranging from 400 to 4000 $\mu$m. The lower limit of the porosity of the ceramic body may be 40%, or even as high as 50% or 70%.

The above properties make the ceramic body highly suitable for use as a scaffold in tissue engineering. In this regard, the term tissue engineering is intended to refer to any process wherein cells are seeded onto the scaffold material and cultured there, either in vitro or in vivo, to form tissue of a desired type. For the formation of tissue, cells of various types may be used ranging from stem cells to all sorts of differentiated cells. Due to its mechanical properties, the present porous ceramic body is particularly useful for tissue engineering bone tissue or for repair of defects at non-load bearing sites, but also at load bearing sites.

It has furthermore been found that the present ceramic body may be crushed to form a granulate of a desired porous structure. The granulate so obtained may find application in for example oral surgery and plastic surgery of the face, as well as in spine surgery and orthopedics. Preferably, the mean diameter of the particles of the granulate are between 2 and 3.5 mm.

The invention will now be elucidated by the following, non-restrictive example.

EXAMPLE

Chemicals Used:

Hydroxylapatite powder (HA), Merck

Polymethylmethacrylate (PMMA)

Carboxy methylcellulose (CMC)

DOLAPIX dispersant from Zschimmer & Schwarz Gmbh

Amonia solution (25%) Merck

Polymethylmethacrylate (PMMA) powder (Dental Biolux International)

Methylmethacrylate (MMA) monomer

Dibenzoylperoxide (DBPO, usually of 75% purity)

N,N dimethyl-p-toluidine (DMPT).

A slurry was prepared by admixing the ingredients listed in table 1 in the specified amounts. Stirring was continued until a homogeneous slurry was obtained.

TABLE 1

Composition of HA slurry

| Ingredient | Quantity (g) | Weight (%) |
|---|---|---|
| Demi-$H_2O$ | 49 | 28.6 |
| $NH_4OH$ (25%) | 4.5 | 2.6 |
| DOLAPIX CE 64 dispersant | 2.5 | 1.5 |
| HA calcined | 115 | 67.1 |
| CMC | 0.26 | 0.15 |
| Total | 171.2 | |

An organic phase was prepared by mixing a powder and a liquid component in respective amounts of 9.3 grams and 3.7 grams. The components were added to each other in a Teflon beaker and stirred until a homogeneous mixture was obtained. The nature of both components is specified in table 2.

TABLE 2

Composition of PMMA

| Component | |
|---|---|
| POWDER component | PMMA Powder + 1% Dibenzoylperoxide (DBPO, usually of 75% purity) |
| LIQUID component | Methylmethacrylate (monomer) + 2% N,N dimethyl - p - toluidine (DMPT). |

Next, 35.0 grams of the HA slurry and the organic phase were mixed under moderate stirring. The volume ratio of HA slurry to organic phase was 6:4. The organic phase was allowed to set at room temperature (RT). The resulting composite green body was dried in air for 6 hours.

Finally, the dried composite green body was placed in a furnace and heated and sintered according to the heating profile shown in FIG. 1.

Figure 2:
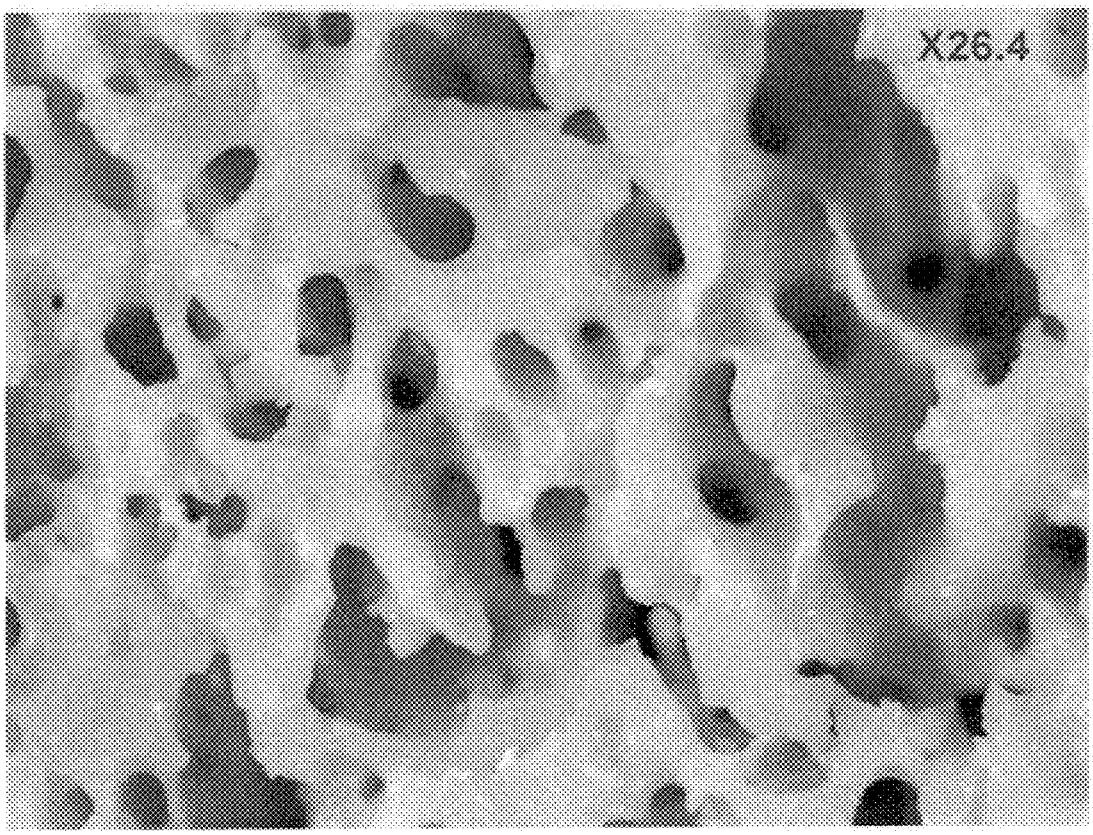
FIG. 2 shows a microscopic photograph (magnification of 26.4) of a body produced in accordance with the embodiment of FIG. 1.
Figure 3:
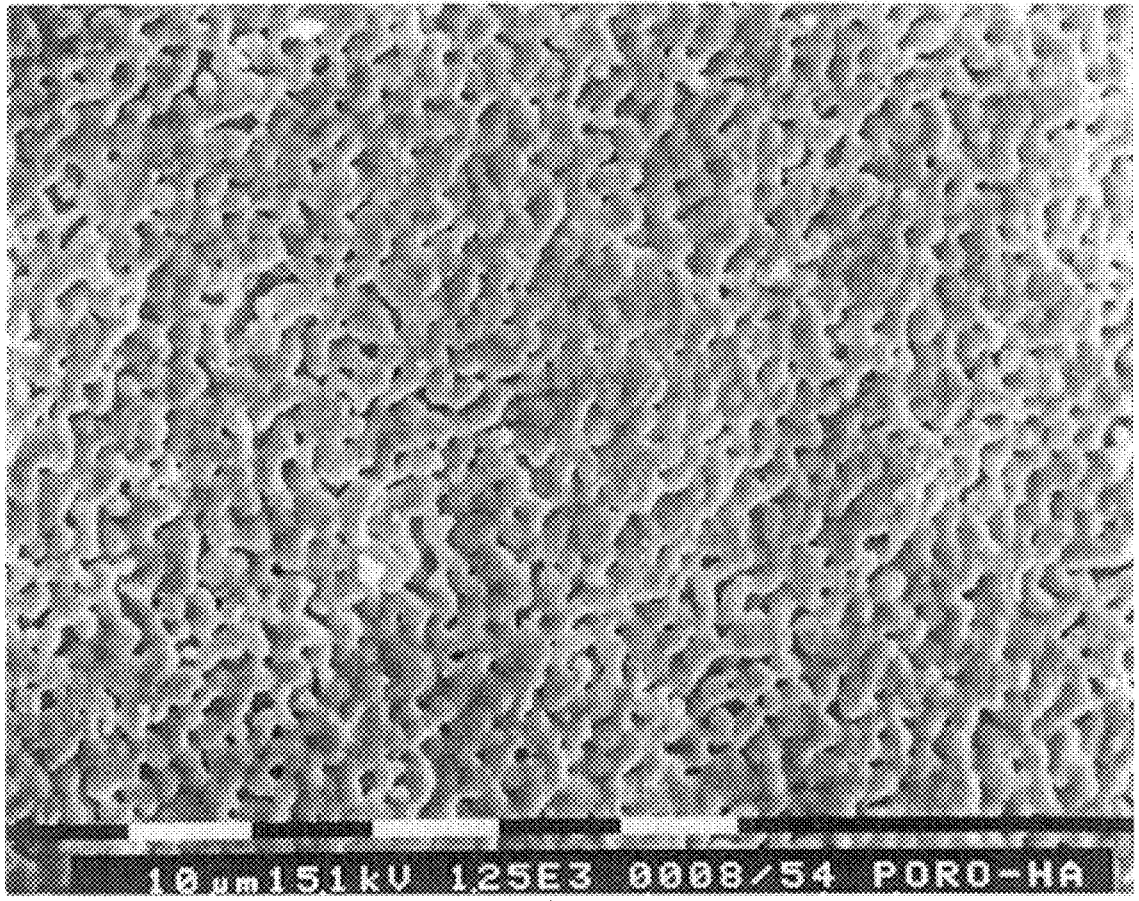
FIG. 3 shows a microscopic photograph (magnification of 1250) of a body produced in accordance with the embodiment of FIG. 1.
Figure 4:
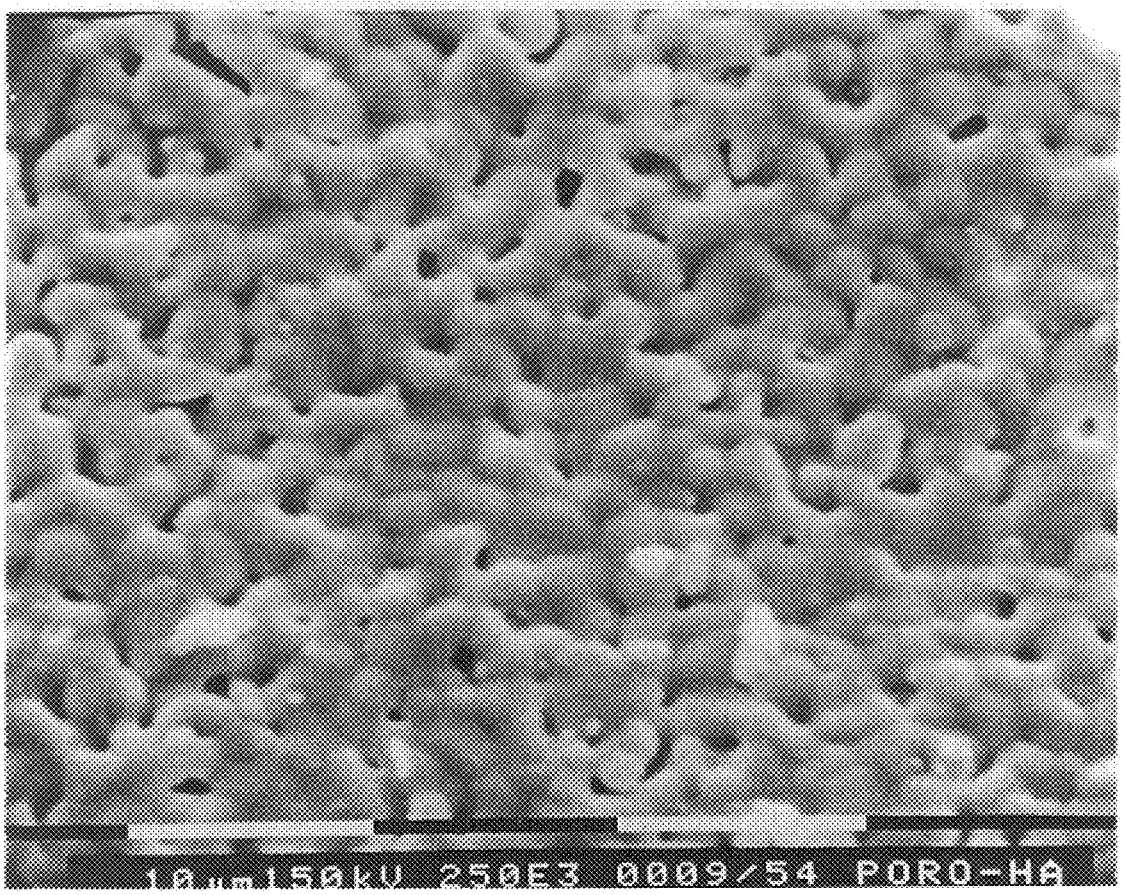
FIG. 4 shows a microscopic photograph (magnification of 2500) of a body produced in accordance with the embodiment of FIG. 1.

Of the obtained ceramic body, microscopic photographs were taken which are shown in FIGS. 2, 3 and 4. FIG. 2 shows the structure under an optical microscope with a magnification of 26.4. FIG. 3 shows the microstructure of the ceramic body within the pores at a magnification of 1250, and FIG. 4 shows the same microstructure at a higher magnification (2500).

What is claimed is:

1. A process for preparing a porous ceramic body comprising the steps of:
   1) preparing an aqueous slurry of a ceramic material;
   2) mixing the slurry with a liquid, viscous organic phase to obtain a dough, wherein the organic phase is substantially insoluble in water, and is thermally decomposable into gaseous residues;
   3) drying the dough; and
   4) removing the organic phase by thermal decomposition.

2. A process according to claim 1, wherein the ceramic material is a calcium phosphate.

3. A process according to claim 2, wherein the calcium phosphate is selected from the group consisting of octacalcium phosphate, apatites, whitlockites, $\alpha$-tricalcium phosphate, $\beta$-tricalcium phosphate, sodium calcium phosphate, and combinations thereof.

4. A process according to claim 1, wherein the slurry comprises between 50 and 80 wt. % of ceramic material, based on the weight of the slurry.

5. A process according to claim 1, wherein the organic phase comprises a material selected from the group consisting of waxes, shellac, fatty acids, fats, epoxy resins, polyurethane resins, polyester resins, poly(meth)acrylate resins, and combinations thereof.

6. A process according to claim 5, wherein the organic phase comprises a poly(meth)acrylate resin.

7. A process according to claim 1, wherein viscosity of the organic phase increases upon drying.

8. A process according to claim 6, wherein the organic phase comprises polymethylmathacrylate, methylmethacrylate and a polymerizing initiator.

9. A process according to claim 1, wherein the dough is dried for at least 5 hours under atmospheric conditions.

10. A process according to claim 1, wherein the organic phase is removed at a temperature of between 200 and 800° C.

11. A process according to claim 1, wherein the porous ceramic body is sintered at a temperature of between about 800 and about 1400° C.

* * * * *